United States Patent
Choi et al.

(10) Patent No.: US 12,042,787 B2
(45) Date of Patent: Jul. 23, 2024

(54) NICKEL-BASED OLIGOMERIZATION CATALYSTS AND METHOD FOR OLIGOMERIZING LIGHT OLEFINS USING THE SAME

(71) Applicants: SK Innovation Co., Ltd., Seoul (KR); SK Geo Centric Co., Ltd., Seoul (KR)

(72) Inventors: Jae Suk Choi, Daejeon (KR); Ka Young Kim, Daejeon (KR); Hee Soo Kim, Daejeon (KR); Ju Hwan Im, Busan (KR); Dae Hyun Choo, Asan-si (KR); Ho Won Lee, Daejeon (KR); Je Mi Lim, Daejeon (KR)

(73) Assignees: SK Innovation Co., Ltd., Seoul (KR); SK Geo Centric Co., Ltd., Seoul (KR)

( * ) Notice: Subject to any disclaimer, the term of this patent is extended or adjusted under 35 U.S.C. 154(b) by 422 days.

(21) Appl. No.: 17/297,522

(22) PCT Filed: Nov. 29, 2019

(86) PCT No.: PCT/KR2019/016718
§ 371 (c)(1),
(2) Date: May 27, 2021

(87) PCT Pub. No.: WO2020/111865
PCT Pub. Date: Jun. 4, 2020

(65) Prior Publication Data
US 2022/0008900 A1    Jan. 13, 2022

(30) Foreign Application Priority Data
Nov. 30, 2018    (KR) ................. 10-2018-0152399

(51) Int. Cl.
| | |
|---|---|
| *B01J 29/04* | (2006.01) |
| *B01J 29/035* | (2006.01) |
| *B01J 35/61* | (2024.01) |
| *B01J 35/63* | (2024.01) |
| *B01J 35/64* | (2024.01) |
| *B01J 37/08* | (2006.01) |
| *B01J 37/30* | (2006.01) |
| *C07C 2/12* | (2006.01) |

(52) U.S. Cl.
CPC ......... *B01J 29/044* (2013.01); *B01J 29/0356* (2013.01); *B01J 35/615* (2024.01); *B01J 35/617* (2024.01); *B01J 35/618* (2024.01); *B01J 35/633* (2024.01); *B01J 35/647* (2024.01); *B01J 37/08* (2013.01); *B01J 37/30* (2013.01); *C07C 2/12* (2013.01)

(58) Field of Classification Search
CPC ..... C07C 2/12; C07C 11/02; C07C 2523/755; C07C 2529/04; B01J 37/08; B01J 37/30; B01J 37/0201; B01J 35/10; B01J 35/1042; B01J 35/1019; B01J 35/1028; B01J 35/1038; B01J 35/1061; B01J 35/1023; B01J 35/023; B01J 29/044; B01J 29/041; B01J 29/042; B01J 2229/18; B01J 2229/186; B01J 35/00
USPC ............................................. 502/60, 73, 74
See application file for complete search history.

(56) References Cited

U.S. PATENT DOCUMENTS

| | | |
|---|---|---|
| 3,140,249 A | 7/1964 | Plank et al. |
| 3,140,251 A | 7/1964 | Plank et al. |
| 7,718,569 B2 | 5/2010 | Ng et al. |
| 8,637,722 B2 | 1/2014 | Inoue et al. |
| 2005/0288471 A1 | 12/2005 | Bitterlich et al. |
| 2017/0218283 A1 | 8/2017 | Lilga et al. |

FOREIGN PATENT DOCUMENTS

| | | |
|---|---|---|
| JP | 2007513753 A | 5/2007 |
| KR | 1020050070106 A | 7/2005 |
| KR | 1020110018389 A | 2/2011 |

OTHER PUBLICATIONS

Wojcieszak et al., Nickel containing MCM-41 and AlMCAM-41 mesoporous molecular sieves Characterisitics and activity in the hydrogenation of benzene, Applied Catalysis A: General 268 (2004), 241-253.*

Hartmann et al., "Ethylene Dimerization and Butene Isomerization in Nickel-Containing MCM-41 and AlMCM-41 Mesoporous Molecular Sieves: An Electron Spin Resonance and Gas Chromatography Study", Journal of Physical Chemistry, 1996, pp. 9906-9910, vol. 100, American Chemical Society.

Hulea et al., "Ni-exchanged AlMCM-41—An efficient bifunctional catalyst for ethylene oligomerization", Journal of Catalysis, 2004, pp. 213-222, vol. 225, Elsevier.

Tverdova et al., "Accurate molecular structure of nickel phthalocyanine (NiN8C32H16): Gas-phase electron diffraction and quantum-chemical calculations", Journal of Molecular Structure, 2012, pp. 227-233, vol. 1023, Elsevier.

* cited by examiner

*Primary Examiner* — Elizabeth D Wood
(74) *Attorney, Agent, or Firm* — The Webb Law Firm

(57) ABSTRACT

In the present disclosure, a heterogeneous nickel-based oligomerization catalyst in which nickel in the form of single atom is loaded on an Al-mesoporous silicate support by ion exchange and a method for producing the same, and a method for oligomerizing light olefins, specifically C4 olefins using the catalyst are described.

13 Claims, 4 Drawing Sheets

NICKEL-BASED OLIGOMERIZATION CATALYSTS AND METHOD FOR OLIGOMERIZING LIGHT OLEFINS USING THE SAME

CROSS-REFERENCE TO RELATED APPLICATIONS

This application is the United States national phase of International Application No. PCT/KR2019/016718 filed Nov. 29, 2019, and claims priority of Korean Patent Application No. 10-2018-0152399 filed Nov. 30, 2018, the disclosures of which are hereby incorporated by reference in their entirety.

BACKGROUND OF THE INVENTION

Field of the Invention

The present disclosure relates to nickel-based oligomerization catalysts and a method for oligomerizing light olefins using the same. More specifically, the present disclosure relates to a nickel-based oligomerization catalyst in which nickel in the form of single atom is loaded on an Al-mesoporous silicate support by ion exchange and a method for producing the same, and a method for oligomerizing light olefins, specifically C4 olefins using the catalyst.

Description of Related Art

It is known that light olefins are generally synthesized by catalytic cracking in petrochemical processes or may be produced through the dehydrogenation reaction of light paraffins. The oligomerized product of these light olefins is used as specialty chemical intermediates such as surfactants and plasticizers as well as transportation fuels such as gasoline and diesel.

Currently, as the commercially available oligomerization process, Axens AlphaButol® process, Chevron Phillips' 1-hexene production process, and the like are mainly known as an ethylene oligomerization process. A homogeneous catalyst in the form of a complex using cobalt, nickel, titanium, or the like as an active metal is used. However, when using a homogeneous catalyst, not only a complicated separation process is required after the oligomerized product is produced but also it is difficult to separate the homogeneous catalyst from the product. Moreover, it is disadvantageous in terms of recycling. Thus, there is an increasing interest in the oligomerization process of olefins using a heterogeneous catalyst.

Among the light olefins, C4 olefins (butene or butylene) are basic compounds widely used as various chemicals and intermediates and are currently available in large quantities from a variety of sources such as Fischer-Tropsch synthesis, butane dehydrogenation reaction, and so on. In this regard, it has emerged as the most efficient method to convert excessively existing C4 olefins into liquid fuel oil through oligomerization reaction. As such, the areas to which the oligomerization of light olefins applies are continuously expanding, in particular, oligomers having an increased number of carbon atoms (specifically, olefins having 8 or more carbon atoms, particularly olefins having more than 8 carbon atoms) are applicable as transportation fuels (for example, aviation fuel, diesel oil), considering the carbon number range thereof, and related research activities and competition in this industry are intensifying.

As a technology for converting light olefins into fuel oil via oligomerization, representatively, UOP's "InAlk" and the like have been commercialized. There, acid catalysts, particularly ion exchange resins such as sulfonated resins or other solid acid catalysts such as solid phosphoric acid (SPA) are used. However, solid acid catalysts such as SPA cause problems related to environmental pollution and difficulties in regeneration of waste catalysts, and thus studies on zeolite-based oligomerization catalysts as a solid catalyst also have recently been actively carried out. In particular, a technology for conducting an oligomerization reaction in the presence of a heterogeneous catalyst in which nickel as an active metal is supported on zeolite (e.g., zeolite beta) or silica-alumina having acid sites has also been developed (for example, US Patent Publication No. 2017-0218283). As for such a nickel-supported catalyst, C4 and C6 olefins are generated at the active sites of nickel, and isomerization proceeds by the adjacent acid sites. However, the deactivation phenomenon of catalyst is caused by acid properties. Further, a catalyst for oligomerization of ethylene in which nickel as an active metal is supported on a silica-alumina support is also known (Korean Patent No. 1250627). However, not only the amount of nickel supported should be a remarkably low level (less than 0.1% by weight) for the dispersibility of nickel but also the deactivation phenomenon of catalyst as described above is inevitable because of the acidic properties of the silica-alumina support.

Accordingly, there is a need for a method capable of oligomerizing light olefins with a favorable conversion and an excellent selectivity and further effectively suppressing the deactivation phenomenon stemming from the acidic properties of nickel-supported catalyst.

SUMMARY OF INVENTION

In an embodiment according to the present disclosure, it is intended to provide a nickel-based catalyst capable of effectively suppressing the deactivation phenomenon caused by the acidic properties in conventional nickel-based supported catalysts while exhibiting favorable oligomerization activity and a method for producing the same.

In another embodiment according to the present disclosure, it is intended to provide a process for producing oligomerization products having an increased number of carbon atoms, further oligomers applicable to transportation fuel oils such as aviation fuel and diesel oil from light olefins, particularly C4 olefins using a nickel-based catalyst exhibiting improved properties.

Solution to Problem

According to a first aspect of the present disclosure, there is provided a method for producing a heterogeneous oligomerization catalyst, the method comprising:

a) providing a Na-type Al-mesoporous silicate having a Si/Al atomic ratio in a range of 5 to 100 as a support, wherein aluminum (Al) forms acid sites on the mesoporous silicate and $Na^+$ ions are bound to the acid sites;

b) ion exchanging the $Na^+$ ions bound to the acid sites of the Na-type Al-mesoporous silicate with nickel ions using a nickel compound having an oxidation number of 2+, wherein the nickel ions are exchanged with the bound $Na^+$ ions, thereby being bound to the Al-mesoporous silicate; and c) performing heat treatment of the Al-mesoporous silicate containing the exchanged nickel ion, wherein nickel is supported on the support in a form of single atom of Ni and an amount of nickel supported is in a range of 0.1% to 10% by weight.

According to a second aspect of the present disclosure, there is provided a heterogeneous oligomerization catalyst comprising Ni in a form of single atom supported on an Al-mesoporous silicate having a Si/Al atomic ratio in a range of 5 to 100 as a support, wherein an amount of nickel supported in the catalyst is in a range of 0.1% to 10% by weight, an acid amount of the catalyst is less than 50 μmol/g, and a molar ratio of nickel (Ni)/aluminum (Al) is in a range of 0.3 to 1.

According to a third aspect of the present disclosure, there is provided an oligomerization method comprising:

providing a light olefin-containing feedstock;

performing an oligomerization reaction of the light olefin-containing feedstock in presence of a heterogeneous catalyst at a temperature of 200° C. to 350° C. and a pressure of 10 to 50 bar; and recovering an olefin having a higher number of carbon atoms than the light olefin from an oligomerized product, wherein the heterogeneous catalyst is a heterogeneous oligomerization catalyst in which Ni in a form of single atom is supported on an Al-mesoporous silicate having a Si/Al atomic ratio in a range of 5 to 100 as a support, wherein an amount of nickel supported in the catalyst is in a range of 0.1% to 10% by weight, an acid amount of the catalyst is less than 50 μmol/g, and a molar ratio of nickel (Ni)/aluminum (Al) is in a range of 0.3 to 1.

Advantageous Effects of Invention

In the heterogeneous nickel-based catalyst according to an embodiment of the present disclosure, an Al-mesoporous silicate into which a relatively large amount of aluminum (Al) is introduced during its preparation is used as a support, the acid sites or the acid amount of the catalyst is decreased by allowing nickel to bind to the acid sites formed by aluminum via ion exchange, and nickel in the form of single atom forms the active sites for oligomerization. Furthermore, the oligomerization catalyst according to an embodiment has an advantage of effectively overcoming the problems associated with deactivation of the conventional nickel-based oligomerization catalysts, by introducing nickel in the form of single atom into the catalyst by direct ion exchange of Na with Ni and thus significantly diminishing the generation of acid sites, rather than performing ion exchange of Na-type Al-mesoporous silicate into ammonium ($NH_4$)-type Al-mesoporous silicate, followed by ion exchange with Ni.

In particular, in the present embodiment, the technical significance is that the catalyst in which an increased amount of nickel is introduced into an Al-mesoporous silicate in the form of single atom, compared to the nickel content applied to the conventional catalysts exhibits excellent long-term activity maintaining ability during the oligomerization of C4 olefins while most of the existing studies have focused on the oligomerization of ethylene.

The heterogeneous catalyst used in the embodiments of the present disclosure also can be easily separated from the products after the reaction is completed, and thus the problems including inefficiency of the separation process when the conventional homogeneous catalyst is applied can be solved. Furthermore, the oligomerized products obtained using the catalyst is expected to be effectively applied to the production of transportation fuels such as aviation fuel and diesel oil in the future since the yield and selectivity for C8 or higher olefins, specifically, C12 olefins which are of increasing interest in recent years can be improved.

DESCRIPTION OF THE INVENTION

Figure 1:
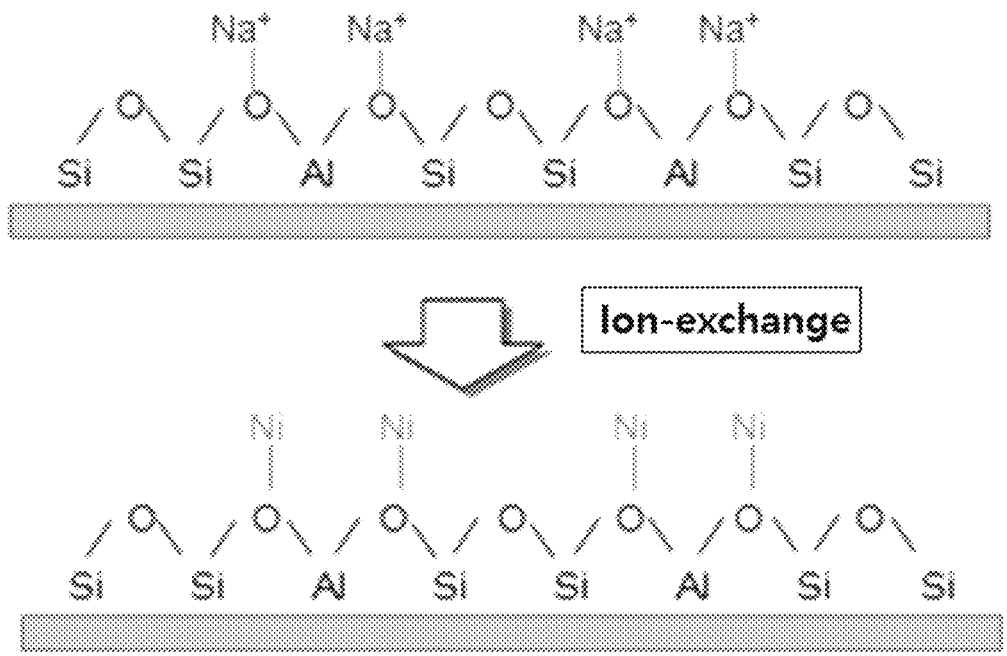
FIG. 1 is a schematic view illustrating the chemical properties of catalytic surface having a decreased number of acid sites, prepared by ion exchange of Na-type Al-mesoporous silicate with nickel according to an embodiment.

The present invention can all be achieved by the following description. The following description should be understood as describing a preferred embodiment of the present invention, and the present invention is not necessarily limited thereto. In addition, it should be understood that the accompanying drawings are provided to aid understanding and the present invention is not limited thereto.

Terms used in the present specification may be defined as follows.

The term "heterogeneous catalyst" refers to a catalyst that is present in a different phase from a reactant in a catalyst reaction process. For example, a heterogeneous catalyst remains undissolved in a reaction medium. When a heterogeneous catalyst is given, the onset of a reaction occurs with the diffusion and adsorption of reactants onto the surface of the heterogeneous catalyst. After completion of the reaction, a product needs to be desorbed from the surface of the heterogeneous catalyst.

The term "support", as used herein, refers to a material (typically a solid-phase material) with a high specific surface area, to which a catalytically active component is attached, and the support may or may not be involved in a catalytic reaction.

The term "active metal" refers to a metallic component directly responsible for progressing a desired reaction of the present disclosure, for instance the oligomerization of light olefins, more specifically the oligomerization of C4 olefins, accounting, together with other components such as a support, for the catalyst.

The term "oligomerization" may refer to a reaction to form oligomers and/or polymers in a broad sense but may refer to a reaction to form an oligomer (for example, olefin) having an increased number of carbon atoms from light olefins (for example, C2 to C5 olefins), other olefins, or any mixture thereof in a narrow sense.

The term "mesoporous silicate (silica)" is an ordered structure synthesized from a silicate precursor in the presence of a structure directing agent (surfactant in the form of a micelle) and specifically may have an amorphous structure ordered on a scale of several nanometers.

The term "C8+ olefin" may mean an olefin having a number of carbon atoms equal to or higher than C8.

Oligomerization Catalyst

As described above, the oligomerization catalyst provided according to an embodiment is a heterogeneous catalyst in which nickel (Ni) in the form of single atom as an active metal is supported on an Al-mesoporous silicate support in which aluminum is introduced into a mesoporous silicate. At this time, aluminum (Al) in the support allows the mesoporous silicate to have acid sites and provides surface areas for supporting nickel (Ni) as active sites in the form of single atom by ion exchange.

The number of such acid sites is increased as the amount of the introduced aluminum increases, and the amount of nickel supported by ion exchange also increases as the amount of the introduced aluminum increases. As a result, the number of acid sites is decreased by the supported nickel, and the catalyst deactivation phenomenon caused by the relatively strong acid sites of the conventional acid catalyst during the oligomerization may be suppressed.

In this regard, the Si/Al atomic ratio in the Al-mesoporous silicate may be in a range of, for example, about 5 to 100, specifically about 7 to 20, more specifically about 10 to 15. At this time, when the Si/Al atomic ratio is too large, the ion exchange site is insufficient and thus the desired amount of nickel may not be supported. When the Si/Al atomic ratio is too small, an excessive amount of nickel is supported on the support or the acid sites are strengthened to act as a deactivation factor of the catalyst. So, it may be advantageous to appropriately adjust the Si/Al atomic ratio in the above range in consideration of the desired amount of nickel supported, the acid properties of the catalyst, and the like. According to a certain embodiment, the Si/Al atomic ratio may be adjusted to 20 or less, particularly 15 or less in the Si/Al atomic ratio range described above in order to maximize the ability to suppress deactivation.

The amount of nickel supported in the form of single atom introduced by ion exchange in the oligomerization catalyst is in a range of, for example, about 0.1% to 10% by weight, specifically about 0.5% to 7% by weight, more specifically 1% to 5% by weight. This is a remarkably higher level as compared to the known nickel content in the conventional high-dispersion nickel-supported catalyst technologies (for example, less than 0.1% by weight as disclosed in Japanese Patent No. 5221659). If the amount of nickel supported is too high, the nickel atoms agglomerate during the preparation process and nickel oxide is generated that does not exhibit the catalytic activity or exhibits decreased catalytic activity. On the other hand, if the amount of nickel supported is too low, a problem may arise that sufficient active sites are not provided and thus the generation speed of oligomers decreases. Considering this, it is advantageous to adjust the amount of nickel supported in the above range.

In particular, it is preferable that the oligomerization catalyst according to the present embodiment contains as little nickel oxide (NiO), particularly nickel oxide in a bulk state as possible. Nickel oxide is acceptable in the form of impurities up to 5% by weight or less, specifically 1% by weight or less. In a particular embodiment, the oligomerization catalyst is substantially free of nickel oxide.

The molar ratio of nickel (Ni)/aluminum (Al) in the catalyst may be in a range of, for example, about 0.3 to 1, specifically about 0.4 to 0.95, more specifically about 0.5 to 0.9. At this time, when the Ni/Al molar ratio is too large, nickel in a bulk form or an oxide form (for example, NiO) may be mixed with nickel in the form of single atom formed by ion exchange, which may adversely affect the catalytic activity. On the other hand, when the Ni/Al molar ratio is too small, the acid sites formed by aluminum (Al) excessively exist, the effect of decreasing the acid sites or acid amount by the introduction of Ni may not be achieved to the desired level, and, as a result, the catalyst deactivation due to acid properties may be caused. Hence, it may be advantageous to appropriately adjust the Ni/Al molar ratio in the above range.

In this manner, nickel is bonded to the Al site of the support by ion exchange and the acid amount of the catalyst decreases, and the acid amount may be, for example, less than about 50 μmol/g, specifically less than about 40 μmol/g, more specifically less than about 30 μmol/g. As the acid amount affects not only the productivity and product distribution of the oligomerized product using light olefins, particularly C4 olefins as the reactant but also the deactivation of the catalyst as described above, it may be advantageous to have the acid amount in the above range.

As such, in the present embodiment, the active sites are nickel (specifically, Ni in the form of single atom), and the oligomerization route may be distinguished from the conventional oligomerization route based on the acid sites.

According to an exemplary embodiment, the nickel-based oligomerization catalyst may have a specific surface area (BET) of about 150 to 1000 $m^2/g$, specifically about 200 to 900 $m^2/g$, more specifically about 300 to 800 $m^2/g$. The pore volume may be in a range of, for example, about 0.2 to 0.5 cc/g, specifically about 0.25 to 0.45 cc/g, more specifically about 0.3 to 0.4 cc/g. In addition, the average pore diameter may be in a range of, for example, about 10 to 35 Å, specifically about 15 to 30 Å, more specifically about 20 to 25 Å and may illustratively have a smaller value than that of the Al-mesoporous silicate support before supporting.

According to an exemplary embodiment, the catalyst may be in the form of a powder, and the particle size (diameter) of the catalyst may be in a range of, for example, about 1 to 500 μm, specifically about 10 to 400 μm, more specifically about 50 to 200 μm, but this may be understood as exemplary meaning. In some cases, the catalyst may be molded into various support shapes known in the art, for example, granules, pellets, tablets, and microspheres. In order to produce the molded catalyst, a binder, for example, alumina or carbon (graphite) may be additionally used. The amount of the added binder may be, for example, up to about 50% by weight, specifically in a range of about 20 to 50% by weight based on the weight of the support.

Method for Producing Oligomerization Catalyst

According to an embodiment, a nickel-based single-atom oligomerization catalyst may be prepared as follows.

First, Na-type Al-mesoporous silicate is prepared as a support (step a).

According to an exemplary embodiment, the Al-mesoporous silicate may be at least one selected from an Al-MCM-based silicate and an Al-SBA-based silicate, specifically at least one selected from Al-MCM-48 or Al-MCM-41, more specifically Al-MCM-48. Unlike zeolite having crystallinity, these materials exhibit amorphous characteristics, but have an ordered structure.

In this regard, the Al-mesoporous silicate may have a specific surface area (BET) of, for example, about 200 to 1200 m$^2$/g, specifically about 250 to 1000 m$^2$/g, more specifically about 300 to 900 m$^2$/g. The pore volume may be in a range of, for example, about 0.3 to 0.6 cc/g, specifically about 0.4 to 0.55 cc/g, more specifically about 0.45 to 0.5 cc/g. In addition, the average pore diameter may be in a range of, for example, about 18 to 40 Å, specifically about 20 to 35 Å, more specifically about 22 to 30 Å. Among these mesoporous silicates, MCM-41 and MCM-48 may have the pore structure and pore size distribution as defined by hexagonal and cubic structures, respectively.

At this time, aluminum may be incorporated by directly adding an aluminum compound in the course of the synthesis of mesoporous silicate or by a post-treatment. In an exemplary embodiment, the aluminum compound (source) may be, for example, an alumina soluble salt, specifically a sodium salt, a chloride, aluminum alcoholate, and the like, more specifically NaAlO$_2$, AlCl$_3$, Al$_2$(NO$_3$)$_3$, NaAl(SO$_4$)$_2$, and the like, and these may be used alone or in combination.

As such, Al-mesoporous silicates, for example, Al-MCM-41 and Al-MCM-48 may be typically prepared, through a hydrothermal synthesis route known in the art, from aluminum sources and silicate sources (for example, tetraalkyl orthosilicate such as TEOS, trade name: Ludox, silicate sol, silica and the like) as the reactants in the presence of a surfactant template or structure directing agent (for example, CTAB (hexadecyltrimethylammonium bromide) or Pluronic series). The hydrothermal synthesis reaction may be conducted at, for example, about 80° C. to 120° C. (specifically about 90° C. to 110° C.) for about 50 to 100 hours (specifically about 60 to 80 hours).

Thereafter, the Al-mesoporous silicate may be obtained through usual subsequent steps such as aging, filtering, washing, drying, and calcination.

As an example, the aging may be carried out at about 80° C. to 120° C. (specifically, about 90° C. to 110° C.) for about 24 to 48 hours (specifically, about 30 to 40 hours). Drying may be performed, for example, under reduced pressure conditions (for example, about 50 to 250 mmHg, specifically about 100 to 150 mmHg) and temperature conditions of about 30° C. to 90° C. (specifically about 40° C. to 60° C.). In addition, calcination may be performed at about 450° C. to 700° C. (specifically about 500° C. to 600° C.) in an oxygen-containing atmosphere (specifically, an air atmosphere). These treatment conditions may be understood in exemplary meaning.

Alternatively, the Al-mesoporous silicate may be prepared by a method in which pure mesoporous silicate is first prepared without incorporation of aluminum and then aluminized using an aluminum compound (for example, (NH$_4$)$_3$AlF$_6$).

According to an embodiment, a hydroxide of an alkali metal, specifically sodium hydroxide or the like may be used as a base component in the aqueous reaction solution when a gel is formed for the synthesis of Al-mesoporous silicate, and the resulting product may be a Na-type Al-mesoporous silicate. In other words, aluminum (Al) may form acid sites on the mesoporous silicate and Na$^+$ ions may be bound or fixed to the acid sites generated by aluminum.

In the afore-mentioned protocol for synthesis of Al-mesoporous silicate, any general descriptions known in the art are omitted.

However, it should be noted that aluminum is incorporated in a larger amount, compared to the conventional ones, for the purpose of introducing a relatively large amount of nickel in the subsequent ion exchange process in the present embodiment. Hence, as described above, the Si/Al atomic ratio may be in a range of, for example, about 5 to 100, specifically about 7 to 20, more specifically about 10 to 15. In this manner, the Bronsted acid sites and/or Lewis acid sites are formed by substituting a tetravalent silicon atom with a trivalent aluminum atom in a tetrahedral structure, and such an acid sites or acid amount may be decreased by nickel introduced by ion exchange.

Next, a step of exchanging Na$^+$ ions bound to the acid sites of the Na-type Al-mesoporous silicate with nickel ions may be carried out (step b).

By way of example, the surface chemistries (state) of the catalyst having a decreased number of acid sites by ion exchange of Na-type Al-mesoporous silicate with nickel are schematically illustrated in FIG. 1.

In this case, the source of nickel ion may be a compound containing a divalent Ni ion (Ni$^{2+}$), more specifically a water-soluble nickel (II) salt and may be, for example, nickel nitrate, nickel sulfate, nickel phosphate, nickel halide, nickel carboxylate, nickel hydroxide, or nickel carbonate, and these may be used alone or in combination. More specifically, nickel nitrate may be used. Typically, the ion exchange reaction may be conducted by bringing the Al-mesoporous silicate into contact with a solution (specifically an aqueous solution) containing a salt of the desired ion to be exchanged. Details of representative ion exchange reactions are described in numerous documents including U.S. Pat. Nos. 3,140,249 and 3,140,251, each disclosure of which is incorporated by reference herein in their entirety.

Referring to FIG. 1, cations (sodium cations) of the outer structure of the synthesized Na-type Al-mesoporous silicate are exchanged with nickel ions (Ni$^{2+}$) by ion exchange. In order to load an active metal on a support, the conventional two-step ion exchange route is carried out such that Na ions of a Na-type inorganic oxide are exchanged with an ammonium salt to completely remove residual Na, followed by calcination for conversion into H$^+$ ions, and then ammonium ions are exchanged with metal ions to be supported. However, after the exchange of ammonium ions, acid sites may be generated or remain during the calcination. In contrast, as for the present embodiment, the exchanging or substituting step with ammonium ion may be omitted, and instead sodium ions present on the support are directly replaced with nickel ions. As a result, the acid amount may be effectively decreased by the introduction of nickel.

According to an exemplary embodiment, the nickel concentration in the aqueous solution of the nickel compound (source or precursor) used for ion exchange may be in a range of, for example, about 0.01 to 10 M, specifically about 0.05 to 5 M, more specifically about 0.1 to 1 M. The ion exchange temperature may be chosen in a range of, for example, about 50° C. to 100° C., specifically about 60° C. to 90° C., and more specifically about 70° C. to 85° C.

As described above, nickel ions (Ni$^{2+}$) are bound or fixed on the support in the form of single atom through ion exchange with Na$^+$ ions on the Al-mesoporous silicate. At this time, nickel ions substitute most of the Na$^+$ ions present on the support. Illustratively, at least about 95%, specifically at least about 99%, more specifically at least about 99.9% of the Na$^+$ ions bound to the acid sites of Na-type Al-mesoporous silicate may be ion exchanged with nickel ions. According to a particular embodiment, substantially all the Na$^+$ ions may be substituted with nickel ions.

As a next step, the Al-mesoporous silicate into which nickel ions (Ni$^{2+}$) have been introduced by ion exchange as described above is subject to heat treatment (step c).

At this time, the heat treatment temperature may be set in a range of, for example, about 250° C. to 1000° C., specifically about 275° C. to 800° C., more specifically about 300° C. to 600° C. This heat treatment step also may be carried out in an oxygen-containing atmosphere. The oxygen-containing atmosphere may be oxygen (specifically, molecular oxygen) alone or a combination of oxygen with any inert gas. As such, the inert gas may be helium, nitrogen, argon or any combination thereof. In the particular embodiment, the oxygen-containing atmosphere may be air.

According to an exemplary embodiment, the oxygen-containing atmosphere may be a mixed gas containing oxygen and nitrogen, where the oxygen content may be in a range of, for example, about 10% to 100% by volume, specifically about 15% to 100% by volume, more specifically about 20% to 100% by volume. Alternatively, an oxygen-containing gas flows into the heat treatment apparatus, in which the flow rate of the gas may be in a range of, for example, about 50 to 300 mL/min, specifically about 100 to 200 mL/min.

During the heat treatment, the ion-exchanged nickel ions having an oxidation number of 2+ may be converted into Ni single atoms, and the oxidation number of Ni at this time may be 1+ and/or 2+. While the present disclosure is not bound by a particular theory, this partial reduction (converted into a species having an oxidation number of 1+) mechanism may be described as follows.

The nickel ions having an oxidation number of 2+ are bonded to water molecules by coordinate bond after ion exchange, water molecules are desorbed by the temperature increase during the heat treatment, and the thus desorbed water molecules react with nickel ions having an oxidation number of 2+ to convert these nickel ions into nickel ions ($Ni^+$) having an oxidation number of 1+ as presented in Scheme 1 below.

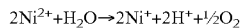

$$2Ni^{2+}+H_2O \rightarrow 2Ni^{+}+2H^{+}+\tfrac{1}{2}O_2 \qquad \text{[Scheme 1]}$$

However, according to experiments by XANES and the like, the oxidation number of supported Ni may be confirmed in a mixed form of 1+ and 2+, and thus it cannot be concluded that only a specific species is involved in the catalytic reaction.

Oligomerization

According to an embodiment of the present disclosure, the heterogeneous nickel single-atom catalyst may be applied to oligomerization, specifically oligomerization of C4 olefins. In this regard, the catalyst has a relatively large amount of nickel single atoms loaded on the support. This catalyst, however, may be limited to exhibit additional performance improvements in terms of of the oligomerization of ethylene that is a main feedstock in the conventional oligomerization.

Specifically, in the production of oligomers by the Cossee-Alrman mechanism, the β-hydrogen transfer reaction from the intermediate product serves as a rate determining step. In this context, as the monomers such as ethylene have a large number of hydrogen atoms directly bonded to carbon double bonds (vinyl hydrogen; e.g., four hydrogen atoms for ethylene), which may become β-hydrogen in the intermediate product, it is easy to carry out the polymerization and the oligomerization. By contrast, in the case of C4 olefins, the number of hydrogen atoms directly bonded to carbon double bonds decreases to 2 and the reaction rate is expected to decrease accordingly. Furthermore, C8 or higher oligomers having a higher molecular weight as compared to the ethylene oligomerization are generated, and thus an increase in adsorption heat and a decrease in activity due to steric hindrance may be expected.

Taking into consideration the above, in order to achieve an economically feasible catalytic conversion in the oligomerization from C4 olefins among light olefins as in the present embodiment, it would be advantageous to secure a preparation method of catalyst that can increase the amount of nickel supported in the form of single atom as compared to the conventional nickel-based catalyst by lowering the Si/Al ratio, to optimize the reaction conditions, and to conduct the oligomerization in the presence of such a catalyst containing nickel at a high content.

According to an exemplary embodiment, the content of olefins, in particular C4 olefins in the feedstock may be in a range of, for example, at least about 50% by volume, specifically at least about 70% by volume, more specifically at least about 80% by volume and may be a level exceeding about 99% by volume in some cases. By way of example, the feedstock may be the C4 fraction, which is available after 1,3-butadiene is separated from the naphtha cracking process, and may be, for example, C4 raffinate-1 (BBR-1), C4 raffinate-2 (BBR-2), and C4 raffinate-3 (BBR-3). In this regard, the content of hydrocarbons other than olefins, in particular paraffins (for example, C4 paraffins) in the feedstock may be, for example, about 20% by weight or less, specifically about 10% by weight or less.

In the present embodiment, the oligomerization proceeds as the feedstock comes into contact with the oligomerization catalyst, the oligomerized product may be converted into hydrocarbons (olefins) having an increased number of carbon atoms by reacting with olefins in the feedstock and/or other oligomerized products, and various kinds of olefins may be contained in the oligomerized product.

According to an exemplary embodiment, the oligomerization catalyst may be contained in a liquid medium (solvent) in the reaction system, the feedstock (for example, gaseous feedstock) containing light olefins, specifically C4 olefins may be charged into the reaction system or reactor, and the reaction may be conducted under the increasing temperature conditions. At this time, the liquid medium may be a hydrocarbon-based organic solvent, and may be, for example, hydrocarbons having single bonds such as undecane, nonane, or heptane or any mixture thereof, and the amount of catalyst in the liquid medium may be adjusted in a range of, for example, about 0.001 to 0.1 g/mL, specifically about 0.005 to 0.05 g/mL, more specifically about 0.01 to 0.03 g/mL.

According to an embodiment, the oligomerization may be conducted at, for example, about 150° C. to 350° C., specifically about 180° C. to 320° C., more specifically about 200° C. to 300° C. In this regard, it may be advantageous to adjust the reaction temperature in the above range since an increase in unreacted substances or deactivation of the catalyst may be promoted when the reaction temperature is too low or high.

The pressure for the oligomerization may be adjusted under partial pressure conditions of the reactant (specifically, light olefins) of, for example, about 10 to 50 bar, specifically about 20 to 45 bar, more specifically 30 to 40 bar. The reaction conditions described above may be understood by way of example and can be changed depending on the kind and concentration of olefins in the feedstock.

According to another embodiment, the oligomerization may be conducted in a continuous mode, and for example, a fixed bed reactor or a semi-batch reactor may be used. At this time, the gas hourly space velocity may be adjusted in a range of, for example, about 0.5 to 10 hr$^{-1}$, specifically about 1 to 8 hr$^{-1}$, more specifically about 2 to 4 hr$^{-1}$, but this may be understood as exemplary meaning.

The product obtained by the oligomerization described above may contain C8 or higher olefins, specifically C12 or higher olefins. In particular, in case of the oligomerized product of C4 olefins, the product may be mostly oligomers having an even number of carbon atoms in light of the nature of the reaction.

In this regard, according to an exemplary embodiment, the productivity of oligomers produced by conducting the reaction in the presence of the catalyst described above may be in a range of, for example, at least about 0.1 $g_{oligo.} \, g_{cat.}^{-1}$ hr$^{-1}$, specifically about 0.2 to 1 $g_{oligo.} \, g_{cat.}^{-1}$ hr$^{-1}$, more specifically about 0.3 to 0.5 $g_{oligo.} \, g_{cat.}^{-1}$ hr$^{-1}$.

When the oligomerization is completed, the resulting oligomers (specifically, olefins having an increased number of carbon atoms) may be separated from the reaction product and recovered. This separation process is known in the art and may be performed by, for example, distillation utilizing the boiling point, adsorption, solvent extraction, and the like.

In particular, the heterogeneous nickel-based single-atom catalyst described above not only increases the yield of the oligomerized product but also has an advantage of being able to increase the fraction of C8 or higher oligomers, specifically C12 or higher oligomers (olefins) having a number of carbon atoms, which is applicable to transportation fuels such as aviation fuel and diesel oil in the oligomerized product. As an example, in the oligomerization of C4 olefins, the fraction of C8 oligomers in the product may be in a range of, for example, about 50% to 90% by weight (specifically, about 60% to 80% by weight) and the fraction of oligomers having a higher number of carbon atoms (C8+ oligomers such as C12 oligomers) may be in a range of, for example, about 10% to 50% by weight (specifically, about 20% to 40% by weight).

According to a particular embodiment, in the oligomerization reaction process, the conversion rate and the selectivity for oligomers (particularly C8+ oligomers) may be, for example, at least about 60% (specifically at least about 70%) and at least about 20% (specifically at least about 30%), respectively.

The present invention may be more clearly understood by the following Examples, and the following Examples are for illustrative purposes only and are not intended to limit the scope of the present invention.

[Embodiments]

EXAMPLES

In Examples, sample analysis was performed according to the following procedure.

XRD Analysis

For the support and the catalyst, the crystalline phase in the catalyst was identified through XRD (X-ray diffraction) analysis. The sample was analyzed in the form of a powder using an XRD X'pert Pro (Marvern Panalytical Ltd.) analyzer. XRD analysis was performed using an X-ray of 40 kV and 30 mA at a rate of 10°/min in a range of 2-Theta of 10° to 80° at 0.02° step.

ICP Analysis

In order to measure the nickel content supported on the support, the crystalline phase in the catalyst was analyzed through ICP (inductively coupled plasma) method. Into a crucible, 1 g of a sample in the form of a powder accurately weighed was put, and the crucible and the sample were subjected to the measurement of loss of ignition (LOI) for 2 hours at 900° C. To a mixture of nitric acid, hydrochloric acid, and hydrofluoric acid in the predetermined amount, 0.02 g of the ignited sample was added, and the mixture was left at room temperature for 24 hours. Thereafter, the mixture was heated at 110° C. for 4 hours in a hot block, and hydrogen peroxide was continuously added thereto five drops every time until the sample became transparent. When about 1 mL of the transparent sample remained, the sample was diluted 1000 times with distilled water and subjected to the measurement of nickel content by ICP-OES.

BET Analysis

Each of the support and the catalyst was subjected to BET analysis to measure the specific surface area, pore size, and volume of the support and the catalyst. For this, an ASAP2020 (Micromeritics Instrument Corporation) analyzer was used, and the analysis was performed after the pretreatment was performed in a vacuum at 350° C. for 3 hours. The surface area of the sample was calculated using the BET equation, and the total pore volume was determined from the nitrogen adsorption amount at p/p0=0.99 atm.

Temperature-Programmed Reduction (TPR) Analysis

It was confirmed whether nickel in the catalyst existed in the form of single atom through TPR analysis. Autochem II Chemisorption Analyzer (Micromeritics Instrument Corporation) was used. The catalyst was produced in the form of a powder, then the predetermined amount thereof was put into the cell and dried at 300° C. for 3 hours for pretreatment.

Next, after 5% $O_2$/He gas was allowed to flow for 30 minutes, the gas was exchanged with He gas for 30 minutes, and then the temperature was lowered to room temperature. After it was waited until the baseline was stabilized while injecting 7% $H_2$/Ar gas for 50 minutes, the analysis was performed while increasing the temperature to 900° C. at 10° C./min when the baseline was stabilized.

Pyridine IR Analysis

The acid sites of catalyst were analyzed through Pyridine-Infra Red (Pyridine-IR) analysis. After the catalyst was produced in the form of a powder, 25 mg of the catalyst powder was prepared in the form of a pellet. The thus-prepared pellet was mounted on the in-situ cell and dried in a vacuum at 500° C. for 3 hours for pretreatment. Next, 0.5 μl of pyridine was injected, and the injected pyridine was allowed to vaporize and pass through the pellet sample. At this time, the amount of pyridine adsorbed on the sample was analyzed by FT-IR and quantified.

Pyridine was used as an adsorbent for the total acid amount, and 2,6-di-tert butyl pyridine (2,6-DTBPy) was used as an adsorbent for the acid amount of the external surface. The internal acid amount was determined by the difference between the total acid amount and the acid amount of the external surface. The acid amount of the external surface was measured by the same way as in measuring the total acid amount except that only the adsorbent material was changed.

In the present Examples, the acid sites are attained by quantifying the Bronsted acid sites (peak attributed to pyridine adsorbed in a range of 1550 to 1570 cm$^{-1}$) induced by Al and the like but not the Lewis acid sites that may be generated by metallic nickel.

X-ray Absorption Fine Structure (XAFS) Analysis

In order to identify nickel single atoms in the nickel single-atom catalyst and to analyze the changes in the environment around the nickel single atoms, Ni K-edge (8,332.8 keV) X-ray adsorption spectroscopy (XAFS) was performed in the SC beamline (nano-XAFS, 4-20 keV, 1012 photons/sec) of the Pohang radiation accelerator (PAL PLS-II).

The gas was adjusted so that the absorption rate of I0 was 16% and the absorption rate of It+Ir was 85%, and the monochromator was detuned to 70%. All samples excluding the reference (0.1 mm) were measured in charge mode after the powder was filled in a 2 mm slit and flattened.

Example 1

Preparation of AlMCM-48

In a 1 L PE container, 2.24 g of NaOH and 0.30 g of $NaAlO_2$ were added to 360 cc of deionized water and stirred for 30 minutes. Separately, 15.26 g of CTAB was added to 576 cc of deionized water in a 2000 cc beaker, and mixing was performed while gradually heating the resultant mixture to 60° C., and the mixture was divided into three portions and added to the sodium-containing solution three times to prepare a mixed solution.

Next, TEOS (Sigma-Aldrich) was added to the prepared mixed solution three times in a total amount of 20.8 g, the resultant mixture was stirred vigorously for 1 hour, and the mixture was poured into a 2 L autoclave and maintained at 30 rpm and 100° C. for 72 hours.

Thereafter, the resultant product was cooled to room temperature and filtered using filter paper, and then the solid was washed with a sufficient amount of deionized water. Subsequently, the washed solid was vacuum dried at 60° C. overnight and calcined at 550° C. for 3 hours in air flow. As a result, 13.19 g of AlMCM-48 was obtained.

Preparation of Ni-AlMCM-48 Catalyst

A catalyst was prepared according to the following procedure using AlMCM-48 as a support.

To 425 g of deionized water, 103.5 g of nickel nitrate (Samchun Chemical Co., Ltd.) was added to prepare an aqueous nickel nitrate solution. To the aqueous nickel nitrate solution, 13.19 g of AlMCM-48 prepared above was added, followed by mixing at 60° C. for 1 hour. Thereafter, the solid obtained through filtering was treated again in the same aqueous nickel nitrate solution and filtered to obtain a solid.

The obtained solid was vacuum dried at 60° C. overnight and calcined at 550° C. for 3 hours in air flow. As a result, 12.85 g of Ni-AlMCM-48 catalyst was obtained.

Characterization

The results attained by performing nitrogen adsorption evaluation and ICP analysis for each of AlMCM-48 and Ni-AlMCM-48 catalyst synthesized in the present Example are presented in the following Table 1 and FIG. 2.

TABLE 1

| Sample | Si/Al atomic ratio | Specific surface area ($m^2/g$) micro | Ext. | Pore volume (cc/g) | Average pore diameter (Å) | Ni content (% by weight) |
|---|---|---|---|---|---|---|
| AlMCM-48 | 12 | 829.1 817.1 | 12.0 | 0.469 | 22.6 | — |
| Ni—AlMCM-48 | | 700.4 691.3 | 9.1 | 0.383 | 21.8 | 4.95 |

Figure 2:
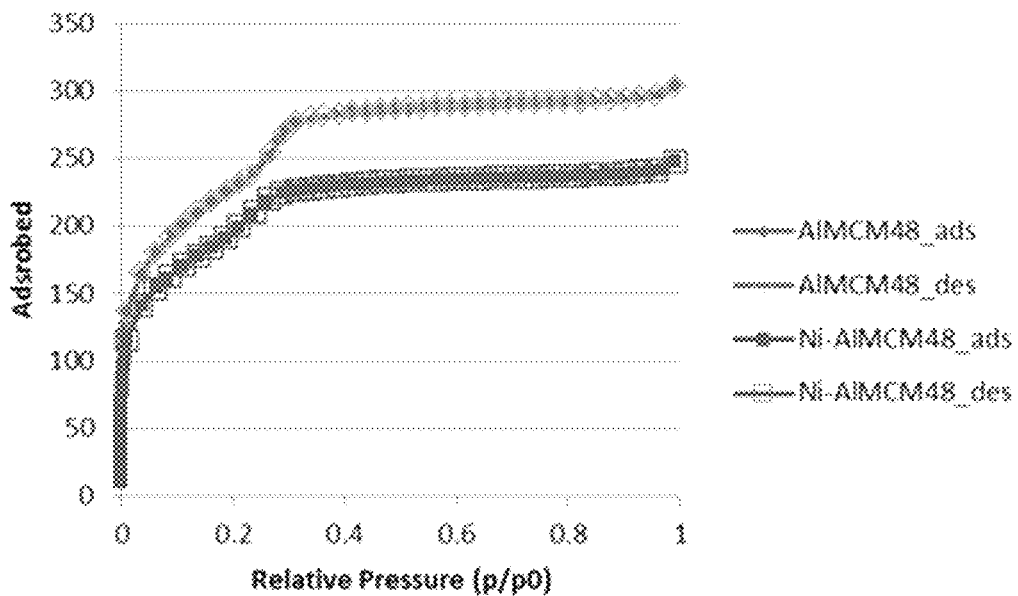
FIG. 2 is a graph illustrating adsorption isothermal curves of AlMCM-48 and Ni-AlMCM-48 catalyst prepared in Examples.

According to FIG. 2, mesopores are well developed even when Al is contained. However, partial decreases in specific surface area and pore volume were observed when nickel (Ni) is supported, but the pore size and specific surface area corresponding to the mesopores were still maintained. In particular, the loaded amount of nickel was 4.95% by weight, which indicates that nickel is supported on the AlMCM-48 support in a relatively high content.

Figure 3:
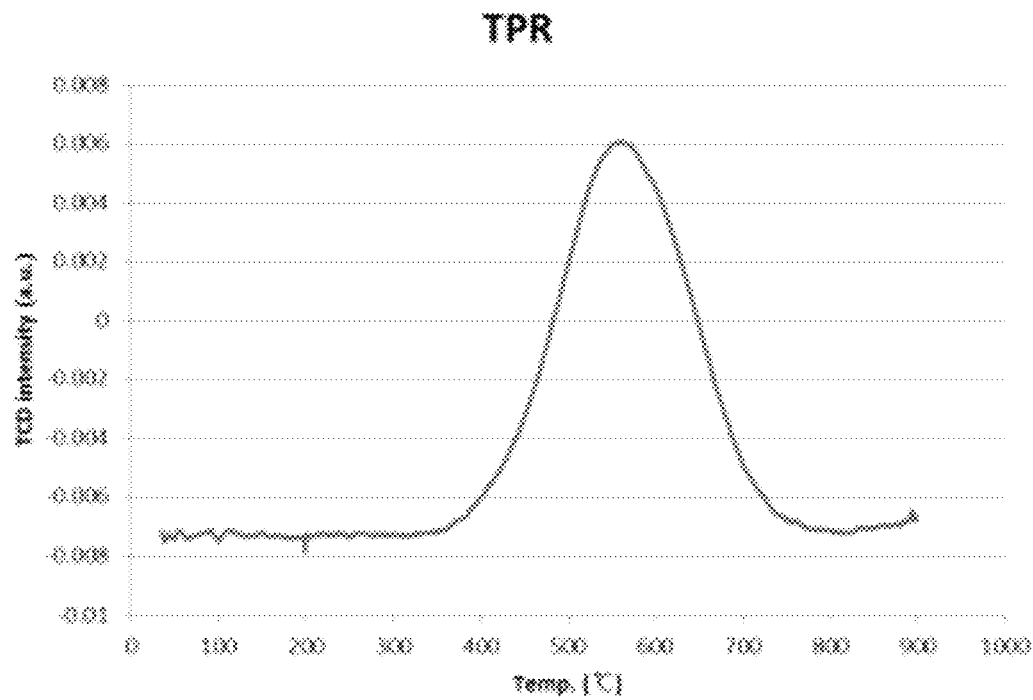
FIG. 3 is a TPR (temperature-programmed reduction) profile of a nickel-based heterogeneous catalyst (Ni-AlMCM-48) prepared in Examples.
Figure 4:
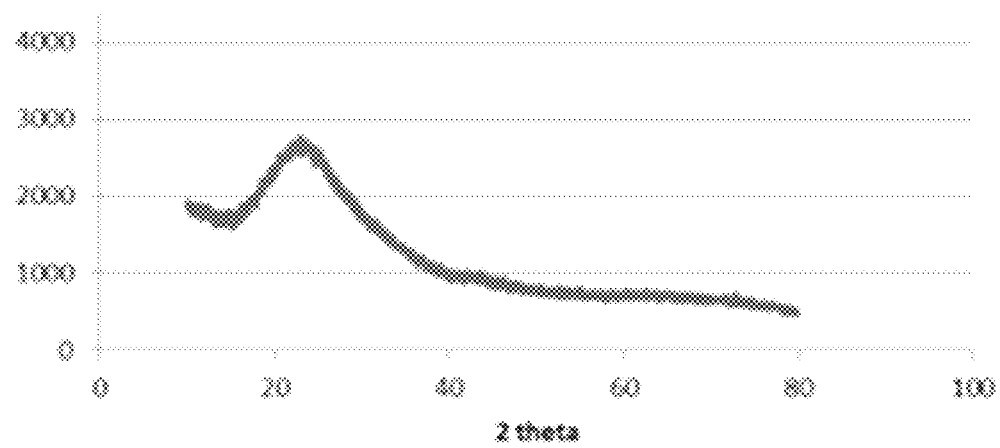
FIG. 4 is a graph illustrating the XRD analysis results of a nickel-based heterogeneous catalyst (Ni-AlMCM-48) prepared in Examples.

Meanwhile, TPR analysis and XRD analysis were performed for the as-prepared Ni-AlMCM-48 catalyst, and the results are illustrated in FIGS. 3 and 4, respectively.

Referring to the drawings, a reduction peak due to nickel oxide is not observed at 250° C. to 400° C. and a reduction characteristic is observed at 500° C. to 700° C., which indicates that nickel does not exist as nickel oxide in a bulk form but as a nickel species that strongly interacts with the silica-alumina support despite the high-temperature calcination conditions.

As a result of XRD analysis, characteristic peaks due to NiO are not observed at 37°, 43°, and 63°. This result means that NiO in a bulk phase does not significantly exist, considering that the nickel content is high in the ICP analysis and the characteristic reduction peak of NiO in a bulk form is not observed as in FIG. 3.

In order to measure the acid amount for each of AlMCM-48 and Ni-AlMCM-48 catalyst, a pyridine infrared spectroscopy (IR) test was performed. According to the test results, the degree of adsorption of pyridine on the Ni-Al-MCM-48 catalyst is remarkably low, which indicates that the Ni-Al-MCM-48 catalyst has a decreased acid amount.

Figure 5A:
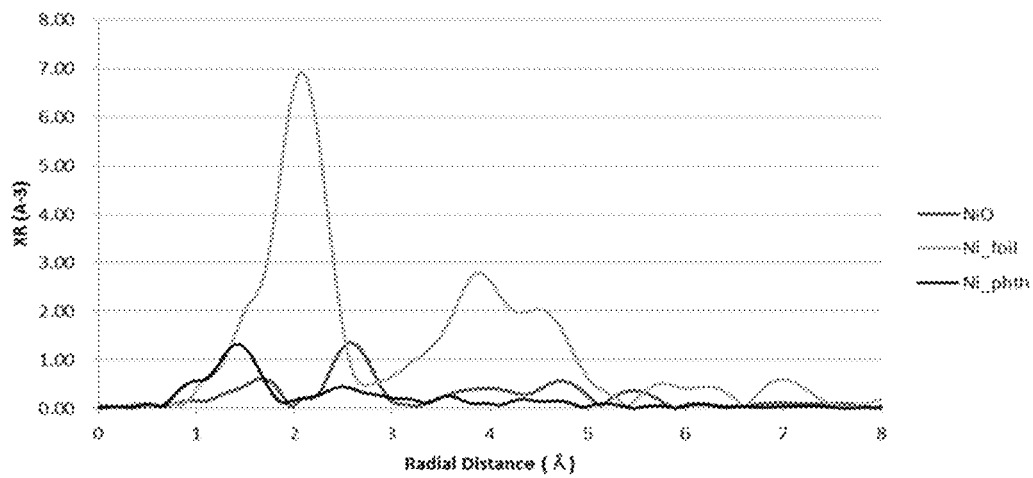
FIGS. 5A and 5B are graphs illustrating XAFS analysis results of a nickel-based heterogeneous catalyst (Ni-AlMCM-48) prepared in Examples, respectively.
Figure 5B:
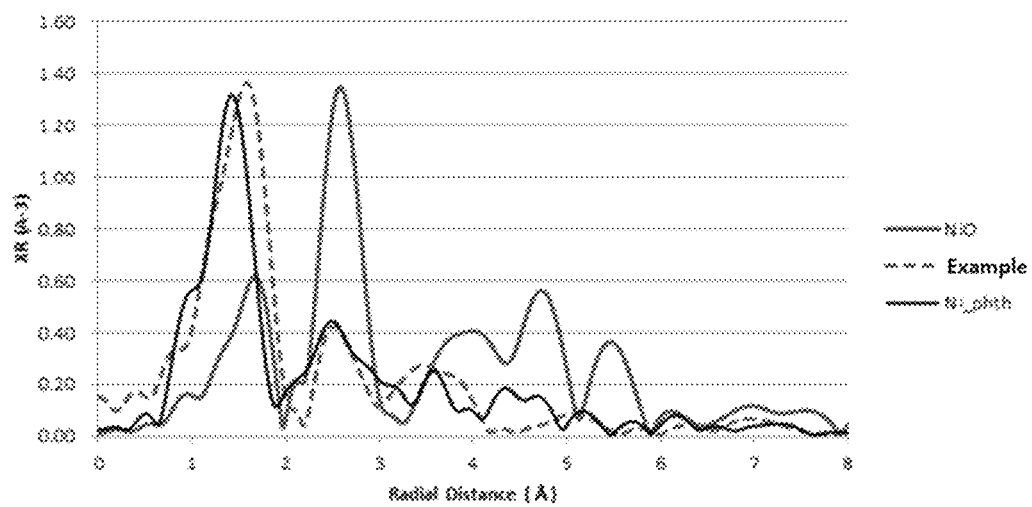

The results of XAFS analysis for the Ni-AlMCM-48 catalyst produced in the present Example are illustrated in FIGS. 5A and 5B, respectively.

FIG. 5A illustrates the results attained by measuring the standard material for each of metallic nickel, nickel oxide, and nickel single atom. The Ni-Ni peak is significantly strongly expressed for the metallic nickel, but the second peak (Ni-Ni) is strongly expressed in addition to the nearest atom (Ni-O) in the case of nickel oxide (NiO). It can be seen that these results are consistent with the respective crystalline structure.

On the other hand, for the nickel in the form of single atom (Ni phthalocyanine), the peak of the nearest atom exists around 1.5 Å and the peaks of the adjacent second and third atoms are significantly diminished. It is confirmed that the structure of nickel (Ni phthalocyanine) is maintained through references (J. Mol. Structure 1023 (2012) 227-233). As such, CN and distribution of Ni metal, NiO, and Ni phthalocyanine are clearly distinguished from one another.

Referring to FIG. 5B, the catalyst according to Example exhibits a similar EXAFS pattern to the isolated nickel, rather than nickel oxide. Thus, it is supposed that the nickel in the catalyst produced according to Example exists in the form of single atom instead of NiO.

Oligomerization

In the present Example, the oligomerization was conducted in the presence of the Ni-Al-MCM-48 catalyst using C4 raffinate-1 (BBR-1; a mixture containing isobutene at 50% by weight, 1-butene at 24% by weight, and 2-butene at 14% by weight) obtained through the separation of the C4 fraction derived from the naphtha thermal cracking process as a feedstock. Separately, the oligomerization (Comparative Example) was conducted using the same catalyst and conditions as those of UOP's InAlk technology for comparison. The process conditions and results are presented in Table 2 below.

TABLE 2

| | Comparative Example | Example |
|---|---|---|
| Catalyst system | SPA (solid phosphoric acid) | Ni—AlMCM-48 |
| Temperature/pressure | 200° C./30 bar | 260° C./30 bar |
| Feedstock (solvent) | BBR-1 (heptane) | |
| C4 = conversion | 90% | 80% |
| Selectivity (yield) | C8 80% (72%)<br>C8+ 20% (18%) | C8 70% (56%)<br>C8+ 30% (24%) |
| Remark | Decrease in conversion is observed (decrease of about 10%) when exposed to 230° C. | Deactivation is not observed even after 20 days |

According to the table, when the oligomerization of C4 olefins according to Example is compared with a commercial process (Comparative Example), the conversion of C4 olefin is somewhat low, but the selectivity for C8+ hydrocarbons, which are hydrocarbons suitable for transportation fuels such as aviation fuel and high-quality solvents, is significantly high. In particular, it is worth noting that the conversion decreases in the commercial process when the reaction temperature is slightly increased for the purpose of maintaining the catalytic activity during the reaction, but deactivation is not observed even after 20 days elapsed in the case of Example.

Figure 6:
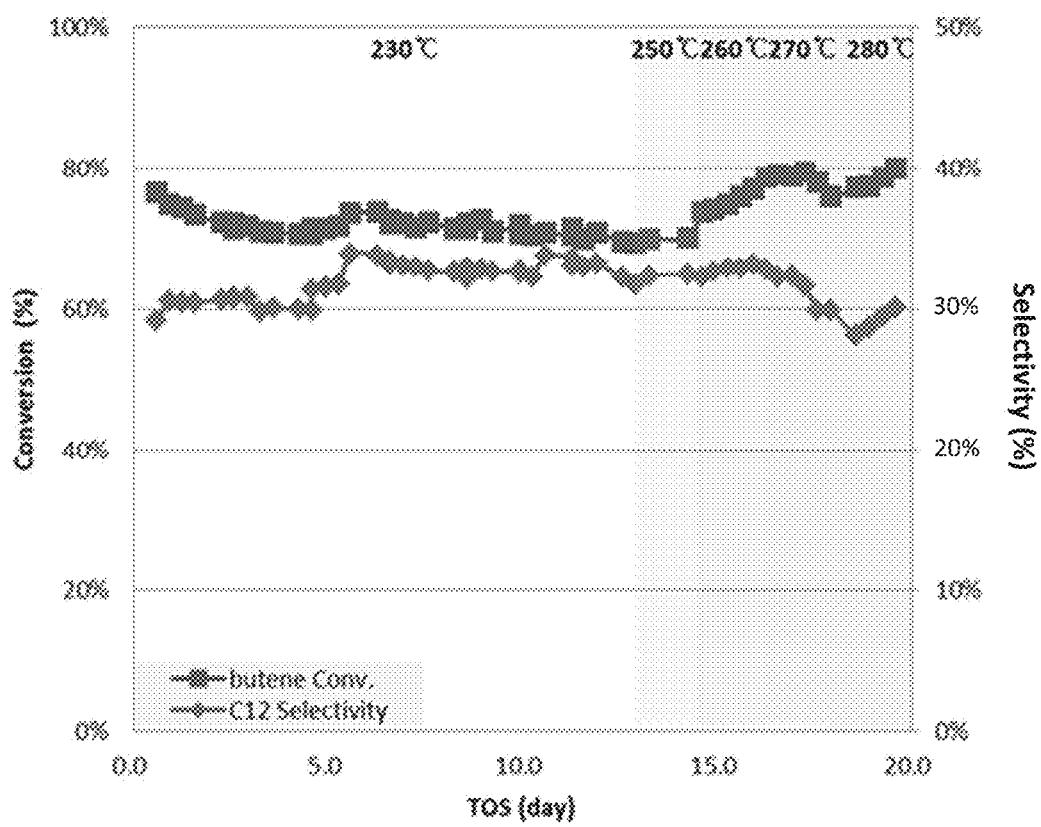
FIG. 6 is a graph illustrating the conversion of butene and selectivity for C12 over time in the oligomerization of C4 olefins conducted in the presence of a nickel-based heterogeneous catalyst (Ni-AlMCM-48) prepared according to Examples.

The butene conversion over time and the selectivity for C12 olefins in the oligomerization according to Example are illustrated in FIG. 6. At this time, the conversion and C12 selectivity were measured while maintaining the temperature at 230° C. until the middle stage of the reaction and then gradually increasing the temperature.

Referring to the drawing, the butene conversion was kept constant at the reaction temperature of 230° C., and the butene conversion also increased as the reaction temperature was increased. However, the C12 selectivity slightly decreased at a reaction temperature of 270° C. or higher and was then gradually recovered.

Considering the above results, the Ni-AlMCM-48 catalyst used in the present Example has favorable deactivation resistance.

Example 2

Evaluation on influence of amount of aluminum incorporated in AlMCM-48 support on oligomerization AlMCM-48 was prepared by the same method as in Example 1 except that the amount of Al incorporated was varied, and Ni-AlMCM-48 catalyst was produced using this as a support. The conversion over time was measured by conducting an oligomerization of C4 fraction under similar reaction conditions (except that the reaction temperature was kept at 230° C.) as in Example 1, and the results are presented in Table 3 below.

TABLE 3

| Si/Al atomic ratio | 20.4 | 15.3 | 12.2 |
|---|---|---|---|
| Initial conversion | 81 | 73 | 76 |
| Conversion after 4 days | 19 | 72 | 72 |

According to the table, the deactivation resistance of the catalyst in which Ni single atoms were loaded on the AlMCM-48 support having a Si/Al atomic ratio of about 15 or less were favorably maintained at the reaction temperature of 230° C.

Further, the conversion significantly decreased after 4 days elapsed as the Si/Al atomic ratio exceeded 20. In other words, the initial activity was high but the catalyst was easily deactivated when the Si/Al atom ratio was high and thus the content of Al that can be substituted with Ni was low. This is supposed to be influenced by the acid strength of Al present in the lattice. In this case, it is required to increase the reaction temperature to a certain level or higher in order to delay the deactivation to some extent.

When the Al content is increased, the activation and the resistance to deactivation are also exhibited to certain levels, but the catalyst tended to be deactivated when Al was excessively added as well. This result is because mesopores for good diffusion of the product are not desirably formed, and the substitution with nickel is insufficiently performed, and thus Al active sites acting as residual acid sites remain.

Example 3

Figure 7:
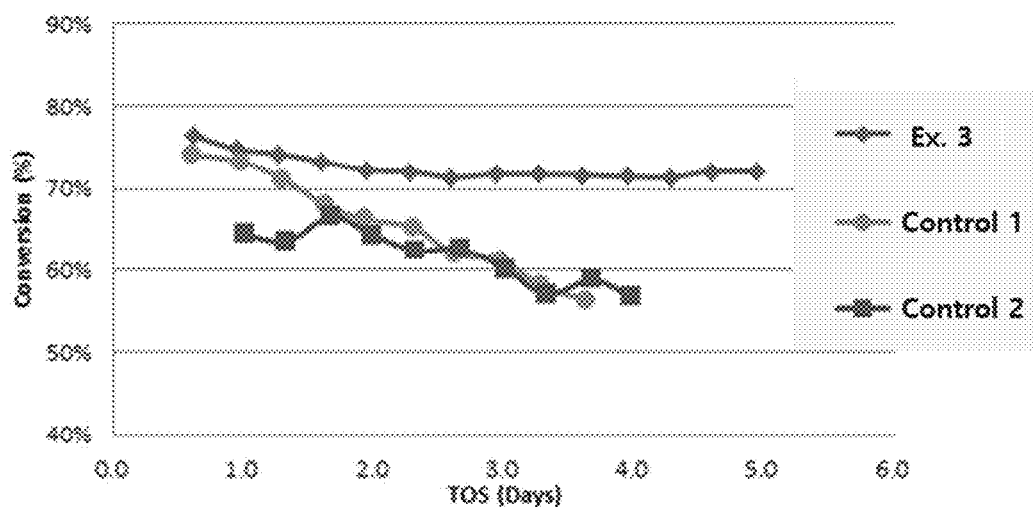
FIG. 7 is a graph illustrating the conversion and selectivity over time in the oligomerization of C4 olefins conducted in the presence of each of a nickel-based heterogeneous catalyst prepared according to Examples and two control catalysts.

The oligomerization was conducted in the presence of the catalyst according to Example (the catalyst having an Si/Al atomic ratio of 12.2 in Table 3) and two kinds of control catalysts. As the control catalysts, zeolite beta (Control 1), and H-Al-MCM-48 (Control 2) that was calcined to maintain the acidity after being substituted with $NH_4NO_3$ without supporting nickel were used. Further, the feedstock was BBR-1, and the reaction conditions were 230° C. and 30 bar. The measurement of the conversion over the oligomerization time are illustrated in FIG. 7.

According to the drawing, for the catalyst according to Example, the conversion did not substantially decrease as the reaction progressed. On the other hand, in the case of the control catalysts, the conversion was equivalent to that in Example at the initial stage, but the conversion all decreased as the reaction progressed.

The amount of Bronsted acid sites measured through the pyridine IR experiment was 22 µmol/g for the catalyst according to Example, but 80 µmol/g for Control 1 and 50 µmol/g for Control 2. These results imply that the control catalysts all have acidic properties and thus are deactivated as the oligomerization proceeds. On the other hand, for the nickel single-atom catalyst used in Example, it is suggested that the deactivation of catalyst due to acidic properties can be effectively suppressed by directly exchanging the sodium ions of Na-type Al-MCM-48 silicate with nickel ions, without any exchange with ammonium ions during the preparation, to substantially suppress the possibility of the acid sites formation.

Simple modifications or changes of the present invention can be easily utilized by those skilled in the art, and all such modifications or changes can be considered to be included in the scope of the present invention.

The invention claimed is:

1. A method for producing a heterogeneous oligomerization catalyst, the method comprising:
   a) providing a Na-type Al-mesoporous silicate having a Si/Al atomic ratio in a range of 5 to 20 as a support, wherein aluminum (Al) forms acid sites on the mesoporous silicate and $Na^+$ ions are bound to the acid sites;
   b) ion exchanging the $Na^+$ ions bound to the acid sites of the Na-type Al-mesoporous silicate with nickel ions using a nickel compound having an oxidation number of 2+, wherein the nickel ions are exchanged with the bound $Na^+$ ions, thereby being bound to the Al-mesoporous silicate; and c) performing heat treatment of the Al-mesoporous silicate containing the exchanged nickel ion, wherein nickel is supported on the support in a form of single atom of Ni and an amount of nickel supported is in a range of 0.1% to 10% by weight, wherein an acid amount of the catalyst is less than 50 μmol/g, and wherein a molar ratio of nickel (Ni)/aluminum (Al) is in a range of 0.3 to 1.

2. The method according to claim 1, wherein at least 95% of $Na^+$ ions bound to acid sites of the Na-type Al-mesoporous silicate is exchanged with a nickel ion in the step b).

3. The method according to claim 1, wherein the Al-mesoporous silicate is at least one selected from an AlMCM-based silicate or an AlSBA-based silicate.

4. The method according to claim 3, wherein the Al-mesoporous silicate is at least one selected from AlMCM-48 or AlMCM-41.

5. The method according to claim 1, wherein the Al-mesoporous silicate has a specific surface area (BET) of 200 to 1200 $m^2/g$, a pore volume of 0.3 to 0.6 cc/g, and an average pore diameter of 18 to 40 Å.

6. The method according to claim 1, wherein the nickel compound having an oxidation number of 2+is at least one selected from the group consisting of nickel nitrate, nickel sulfate, nickel phosphate, nickel halide, nickel carboxylate, nickel hydroxide, and nickel carbonate.

7. The method according to claim 1, wherein a nickel concentration in an aqueous solution of the nickel compound having an oxidation number of 2+used during the ion exchange in the step b) is in a range of 0.01 to 10 M.

8. The method according to claim 7, wherein ion exchange in the step b) is performed at 50° C. to 100° C.

9. The method according to claim 1, wherein the step c) is carried out at 250° C. to 1000° C. in an oxygen-containing atmosphere.

10. The method according to claim 1, wherein the step b) is carried out by directly ion exchanging the $Na^+$ ions of the Na-type Al-mesoporous silicate with nickel ions without passing through an exchange with ammonium ions.

11. The method according to claim 1, wherein the oligomerization catalyst has a specific surface area (BET) of 150 to 1000 $m^2/g$, a pore volume of 0.2 to 0.5 cc/g, and an average pore diameter of 10 to 35 Å.

12. The method according to claim 1, wherein a particle size (diameter) of the oligomerization catalyst is in a range of 1 to 500 μm.

13. The method according to claim 1, wherein the oligomerization catalyst substantially free of nickel oxide (NiO).

* * * * *